United States Patent
Koenig (10) Patent No.: US 8,145,683 B2
(45) Date of Patent: Mar. 27, 2012

(54) DATA STRUCTURE AND METHOD FOR CREATING AND STORING A FILE

(75) Inventor: Helmut Koenig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 436 days.

(21) Appl. No.: 11/080,821

(22) Filed: Mar. 16, 2005

(65) Prior Publication Data

US 2005/0210063 A1  Sep. 22, 2005

Related U.S. Application Data

(60) Provisional application No. 60/553,566, filed on Mar. 17, 2004.

(30) Foreign Application Priority Data

Mar. 17, 2004  (DE) .................. 10 2004 013 132

(51) Int. Cl.
*G06F 7/00* (2006.01)
*G06F 17/30* (2006.01)

(52) U.S. Cl. ......................... 707/804; 707/796
(58) Field of Classification Search .......... 707/3, 103 R, 707/103 Y, 101, 4, 804, 796
See application file for complete search history.

(56) References Cited

U.S. PATENT DOCUMENTS

| | | | | |
|---|---|---|---|---|
| 5,848,410 A | * | 12/1998 | Walls et al. ................. | 707/4 |
| 6,370,536 B1 | * | 4/2002 | Suzuki et al. .............. | 715/234 |
| 6,625,596 B1 | * | 9/2003 | Nunez ......................... | 707/3 |
| 6,654,754 B1 | * | 11/2003 | Knauft et al. .............. | 707/101 |
| 7,155,444 B2 | * | 12/2006 | Krishnan et al. .......... | 707/101 |
| 7,337,297 B2 | * | 2/2008 | Chen et al. ................. | 711/170 |
| 2003/0037312 A1 | * | 2/2003 | Czech ....................... | 717/120 |

OTHER PUBLICATIONS

T. Timpka, L. Padgham, P. Hedblom, S. Wallin, T. Tibblin, A hypertext knowledge based for primary care—LIMEDS in LINCKS, May 1989, ACM SIGIR Forum, Proceedings of the 12th annual international ACM SIGIR conference on Research and development in information retrieval SIGIR '89, vol. 23 Issue SI, ACM Press, pp. 221-228.*

"A Hypertext Knowledge Base for Primary Care—LIMEDS in LINCKS", by Toomas Timpka, Published 1989. http://delivery.acm.org/10.1145/80000/75358/p221-timpka.pdf?key1=75358&key2=8912053221&coll=GUIDE&dl=GUIDE&CFID=5524256&CFTOKEN=31990654.*

(Continued)

*Primary Examiner* — Apu Mofiz
*Assistant Examiner* — Chelcie Daye
(74) *Attorney, Agent, or Firm* — Harness, Dickey & Pierce, PLC (57) ABSTRACT

A data structure is for storing data including a number of files which each have a file header and a file body. The file header of a respective file contains general information with respect to the respective content of the respective file body of the respective file. Further, the file header of a respective first file additionally contains context information with respect to at least one further file, the file body of which exhibits a material reference to the content of the file body of the respective first file. The file structure and a method are proposed for creating and storing a file which allow an observer to determine in a particularly simple manner the volume and content of the information relevant for the file.

16 Claims, 3 Drawing Sheets

OTHER PUBLICATIONS

"A Hypertext Knowledge Base for Primary Care—LIMEDS in LINCKS", by Toomas Timpka, Published 1989. http://delivery.acm.org/10.1145/80000/75358/p221-timpka.pdf?key1=75358&key2=2180057421&coll=GUIDE&dl=GUIDE&CFID=45344964&CFTOKEN=90671545.*

"A Hypertext Knowledge Base for Primary Care—LIMEDS in LINCKS", by: Toomas Timpka, Published 1989. http://delivery.acm.org/10.1145/80000/75358/p221-timpka.pdf?ip=151.207.246.4&acc=ACTIVE%20SERVICE&CFID=64715150&CFTOKEN=39641462&__acm__=1319653691__e869212b5d0c9061209c3979f15590b5.*

Rita Noumeir, "DICOM Sturctured Report Document type Definition", IEEE Transactions on Information Technology in biomedicine, vol. 7, No. 4, Dec. 2003.

HDF User's Guide, Version 4. 1r5, Nov. 2001, NCSA University of Illinois at Urbana-Champaign.

German Office Action issued on Dec. 3, 2004.

\* cited by examiner

DATA STRUCTURE AND METHOD FOR CREATING AND STORING A FILE

The present application hereby claims priority under 35 U.S.C. §119 on German patent application number DE 10 2004 013 132.5 filed Mar. 17, 2004, and on U.S. provisional patent application Ser. No. 60/553,566 filed Mar. 17, 2004, the entire contents of each which are hereby incorporated herein by reference.

FIELD OF THE INVENTION

The present invention generally relates to a data structure for storing data. The present invention furthermore generally relates to a method for creating and storing a first file and/or to a method for the rule-based determination of files relevant in any respective current operating step.

The present invention thus generally relates to a data structure for storing data. Preferably, it relates to one having a number of files which in each case have a file header and a file body, the file header of a respective file containing general information with respect to the respective content of the respective file body of the respective file and the file header of a respective first file additionally containing context information with respect to at least one further file, the file body of which exhibits a material reference to the content of the file body of the respective first file.

BACKGROUND OF THE INVENTION

A data structure is known from the DICOM (Digital Imaging and Communications in Medicine) SR (Structured Reporting) standard. DICOM-SR objects contain references to other DICOM-SR objects in a "DICOM Current Requested Procedure Evidence Sequence" and a "Pertinent Other Evidence Sequence". Both sequences contain hierarchically ordered identifiers which are called DICOM UIDs (unique identifiers). In this context, DICOM UIDs are provided for the "study", "series" and "instance" levels.

The generic publication "DICOM Structured Report Document Type Definition" by Rita Noumeir, IEEE Transactions on Information Technology in Biomedicine, Vol. 7, No. 4, December 2003, discusses the possibility of using the XML text format in conjunction with the DICOM standard.

In objects and files according to the DICOM-SR standard, it is not possible to find a reference to the content of the referenced DICOM-SR objects in the sequences so that somebody viewing the sequences cannot determine why the objects referenced in a sequence are considered to be relevant for the respective DICOM-SR object, without looking at the document content of the referenced object. It is only possible to see that reference was made to the referenced DICOM-SR object.

Furthermore, such data structures are known from the HL7 (Health Level 7) CDA (Clinical Document Architecture) standard. According to this standard, a reference to external references is specified in a respective file body of the respective file.

This standard, too, thus requires the document content of a respective referenced file to be analyzed in order to be able to selectively access objects which are relevant under certain queries or in a particular constellation.

The publication "HDF User's Guide", version 4.1r5 of the University of Illinois in NCSA Scientific Data Technologies of November 2001 proposes a hierarchical data format called HDF. Files according to this format have a data header, a data description section and a section including the data elements. In this context, various types of files can be stored in the section including the data elements. The data description section contains information on the files stored in the section comprising the data elements.

SUMMARY OF THE INVENTION

It is an object of an embodiment of the present invention to provide a data structure and/or a method for creating and storing a file which allow an observer of the data structure or file to determine in a particularly simple manner the number and content of the information relevant for a data structure or file considered in each case.

In a storage medium on which a data structure is stored, an object may be achieved by an embodiment of the invention.

In a method for creating and storing a first file, an object may be achieved by an embodiment of the invention.

According to an embodiment of the invention, the context information, contained in a file header of a respective first file, with regard to at least one further file, the file body of which exhibits a material reference to the content of the file body of the respective first file, includes information on the content of the file body of the respective further file.

As a result, the information stored in the file header of a respective file is extended in such a manner that each file contains detailed information on the context (e.g. procedure and clinical patient context) and associated relevant files. An observer can thus determine why the referenced file was considered to be relevant at the time of the generation of the first file without reading the file content of the referenced file, which file content is stored in the respective file body. This considerably reduces the workload since now only referenced files appearing to be relevant have to be opened.

Furthermore, suitable filters enable data which are relevant in a respective processing step to be selectively deposited and found again. This considerably reduces the time for searching for and selecting relevant data so that the (preferably clinical) data stored in the files of the data structure can be assessed more rapidly.

Since the solution according to an embodiment of the invention is completely autonomous, it represents an advantageous alternative to an archiving system provided centrally on a server. As a result, the data traffic via a network possibly used can be kept down and the transmission times can thus be reduced.

In this arrangement, it is particularly advantageous if the information on the content of the file body of the respective further file, which information is stored in the context information, corresponds to a predetermined reference terminology.

This is made possible by the precise contextual semantics of the referenced files. Furthermore, metadata of the file content of a respective further file, which file content is stored in the respective file body, can be utilized for communicating the information of an interpretation or results context which is contained therein.

It is particularly advantageous if the reference terminology meets the widely used SNOMED standard (Systematized Nomenclature of Medicine).

It is also advantageous if the context information includes at least the file name and/or the storage location of the respective further file and/or identifies the type of file body of the respective further file.

It is particularly advantageous if the context information additionally contains a measure of the respective intensity of the material reference (similarity) of the file body of the respective further file to the content of the file body of the respective first file.

This immediately enables an observer of the first file to determine the relevance of a referenced file.

An object may also be achieved by a method of an embodiment for creating and storing a first file which exhibits a file header and a file body, the method containing the following steps:

generating a file body which contains data to be stored in the first file;

generating a file header which contains general information with respect to the respective content of the respective file body of the respective first file;

automatically detecting at least one access to a file body of at least one further file during the generation or modification of the file body of the first file;

automatically storing the detected accesses as context information in the file header of the first file; and storing the file body together with the file header in a file.

The method according to an embodiment of the invention ensures that each first file created or modified automatically contains a reference to other files which were accessed during the creation of the first file.

It is particularly advantageous in this connection if the context information includes information on the content of the file body of the respective further file since it is thus possible, without reading the file content of the respective further file, to determine the information relevant for referring to the respective further files only by way of the first file.

In this case, it is particularly advantageous if the information on the content of the file body of the respective further file, which information is stored in the context information, is stored in the form of a predetermined reference terminology, the reference terminology preferably meeting the SNOMED standard.

It is also particularly advantageous if the context information includes the file name and/or the storage location of the respective further file and/or identifies the type of file body of the respective further file.

The method according to an embodiment of the invention also exhibits the following steps:

automatically reading out general information with respect to the respective content of the respective file body of the respective further file, which information is stored in a file header of the at least one further file; and automatically storing the general information read out as additional context information in the file header of the first file.

This ensures that the file header of the respective first file automatically contains information on the content of the file body of a referenced second file.

In order to automatically obtain a measure of the respective intensity of the material reference (similarity) of the content of the file body of the respective further file to the content of the file body of the respective first file, it is also advantageous if the method also exhibits the following steps:

automatically determining the duration of the respective access to a file body of at least one further file during the generation or modification of the file body of the first file; and automatically storing the particular duration of the respective access as additional context information in the file header of the first file.

For an automatic rule-based determination of files relevant in a respective current operating step, it is also advantageous if the method also exhibits the following steps:

automatically comparing the information on the content of the file body of the respective further file, which information is stored in the context information of the file header of the currently processed file, with an application context of an application used for processing the currently processed file;

automatically determining a relevance, resulting from the comparison, of the further files with respect to the application context; and automatically opening and/or locally loading the further file or files, the relevance of which exceeds a predetermined threshold value.

BRIEF DESCRIPTION OF THE DRAWINGS

In the subsequent detailed description, exemplary embodiments of the invention will be described in greater detail with reference to the attached drawings, in which identical reference symbols designate identical parts in the views and in which.

DETAILED DESCRIPTION OF THE EXAMPLE EMBODIMENTS

Figure 1:
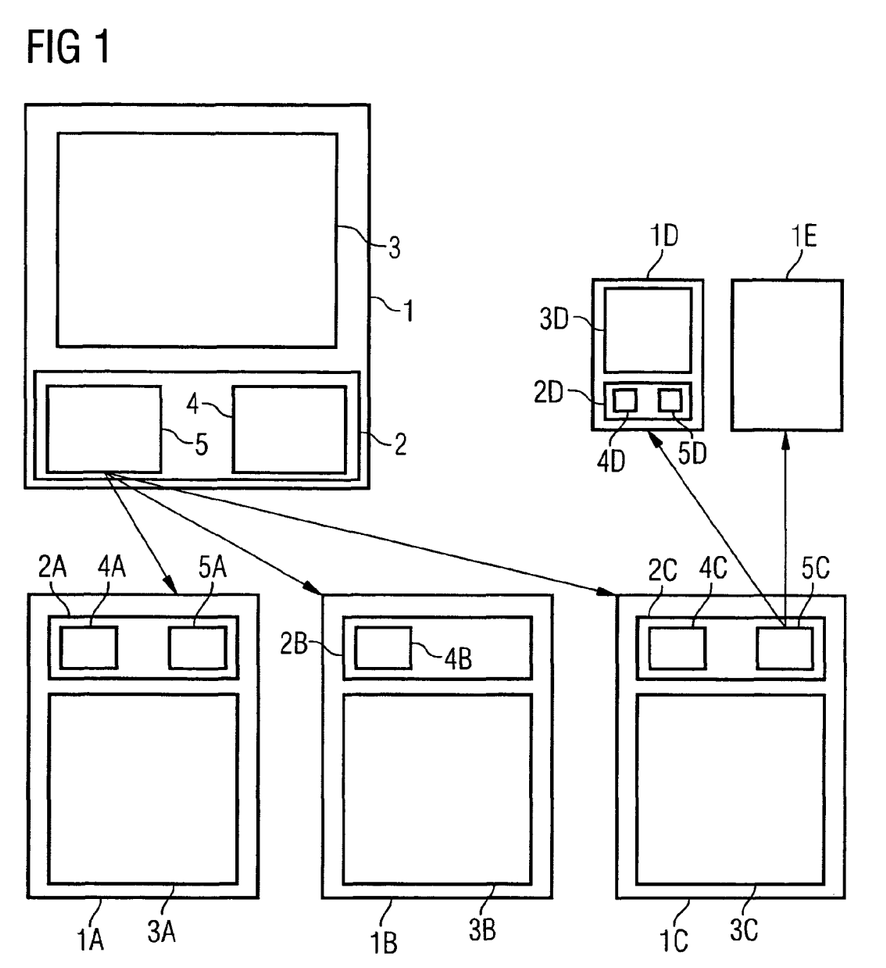
FIG. 1 diagrammatically illustrates the data structure according to an embodiment of the invention.

FIG. 1 diagrammatically shows the data structure according to an embodiment of the invention for storing data.

In this figure, reference symbols 1, 1A, 1B, 1C, 1D and 1E designate various files which can be stored on one or more storage media such as, e.g. a floppy disk, a CD-ROM, a DVD or a hard disk.

The files 1, 1A, 1B, 1C and 1D shown in FIG. 1 in each case have a file header 2, 2A, 2B, 2C and 2D and a file body 3, 3A, 3B, 3C and 3D.

The respective file body 3, 3A, 3B, 3C and 3D of the respective file 1, 1A, 1B, 1C and 1D contains the actual content of the respective file. This content can be, for example, text data, image data, recorded data from medical instruments or any other information.

The file header 2, 2A, 2B, 2C and 2D of the respective file 1, 1A, 1B, 1C and 1D contains, in the particularly preferred embodiment of the present invention, shown in FIG. 1, on the one hand, general information 4, 4A, 4B, 4C and 4D with respect to the respective content of the respective file body 3, 3A, 3B, 3C and 3D of the respective file. This general information can contain, for example, the file name, the file size, the date of creation, the author, commentaries and key words and file attributes (such as write-protected, hidden, archive). In addition, the general information 4, 4A, 4B, 4C and 4D can contain reproduction information which is required for reading and, if necessary, decoding the data stored in the respective file body 3, 3A, 3B, 3C and 3D.

The file header 2, 2A, 2C and 2D of the files 1, 1A, 1C and 1D also contains additional context information 5, 5A, 5C and 5D with respect to at least one further file, the file body of which exhibits a material reference to the content of the file body 3, 3A, 3C and 3D of the respective first file 1, 1A, 1C and 1D. In FIG. 1, the files referenced by the files 1 and 1C are then shown separately.

In real terms, the file header 2 of the file 1 contains in the example shown in FIG. 1 additional context information 5 with respect to files 1A, 1B and 1C since the content of the file bodies 3A, 3B and 3C of the files 1A, 1B and 1C exhibits a material reference to the content of the file body 3 of the first file 1.

The file header 2C of file 1C, in turn, contains context information 5C with respect to the further files 1D and 1E since the content of the file body 3D of file 1D and the content of file 1E exhibits a material reference to the content of the file body 3C of file 1C.

Thus, a file 1C, which has already been referenced in the context information 5 of a file header 2 of a first file 1, can also contain in its file header 2C, context information 5C with respect to one or more further files 1D and 1E. Apart from such a tree structure, referring back from referenced file to the referencing file is also possible.

As file 1E is intended to illustrate, the file referenced in the context information does not need to exhibit the same structure as the respective first file 1C but can itself exhibit an arbitrary structure. Correspondingly, the referenced file 1B exhibits a different structure than the referenced file 1 since the file header 2B of file 1B does not contain any context information.

According to an embodiment of the invention, the respective context information 5 and 5C of the respective referencing files 1 and 1C thus comprises information on the content of the file bodies 3A, 3B, 3C and 3D of the respective referenced files 1A, 1B, 1C and 1D, 1E, which are materially referred to the content of the file body 3 and 3C, respectively, of the respective first referencing file 1 and 1C.

In the particularly preferred exemplary embodiment shown in FIG. 1, the information on the content of file bodies 3A, 3B, 3C and 3D of the respective referenced further files 1A, 1B, 1C and 1D and 1E, which information is stored in the context information 5 and 5C, is stored in accordance with the SNOMED standard.

Storage in accordance with the SNOMED standard enables the precise contextual semantics of the referenced files to be used, which facilitates the use of filtering functions for finding wanted files. Furthermore, metadata of file content of a respective further referenced file can thus be used for communicating the information of the interpretation and results context of the referencing file.

The information, contained in the context information 5A of file 1A, on the content of a file body of a respective further file, not shown in the figure, the content of which exhibits a material reference to the content of the file body 3A of file 1A, is stored in accordance with an alternative predetermined reference terminology.

This makes it clear that the information on the content of file bodies of the files referenced in each case, which information is stored in the context information 5, 5A, 5C and 5D of various referencing files 1, 1A, 1C and 1D, can be stored in accordance with different reference terminologies. Naturally, however, the context information can also be stored in accordance with a uniform standard, which is advantageous.

In FIG. 1, the context information 5, 5A, 5C and 5D of files 1, 1A, 1C and 1D comprises the file name and the storage location of the respective further referenced file 1A, 1B, 1C and 1D and 1E and the type of file body 3A, 3B, 3C and 3D of the respective further file 1A, 1B, 1C and 1D.

Furthermore, the context information 5, 5A, 5C and 5D of the referencing files 1, 1A, 1C and 1D shown in FIG. 1 includes information on relevant places in the files referenced in each case.

This information can, for example, be provided in the form of a specification of the relevant positions in the form of "page/line" in the case of referenced text files and by specifying coordinates in the form of "X/Y" in the case of referenced graphics files.

However, it is clear that the context information, as an alternative, could also contain only a selection of the aforementioned information. In this arrangement, uniformity is advantageous but not mandatory.

In order that an observer can directly see the relevance of a referenced file, the context information 5 of the referencing file 1 also contains a measure of the respective intensity of the material reference of the file body 3A, 3B and 3C, respectively, of the respective further referenced file 1A, 1B and 1C, to the content of the file body 3 of the respective first file 1. This measure can preferably be specified in percent.

Naturally, the context information 5A, 5C and 5D of the further files 1A, 1C and 1D, in turn, can again contain a measure of the respective intensity of the material reference of a file body of a respective further file to the content of the file body 3A, 3C and 3D of the respective first file 1A, 1C and 1D. Here, too, standardization is advantageous but not mandatory.

Figure 2:
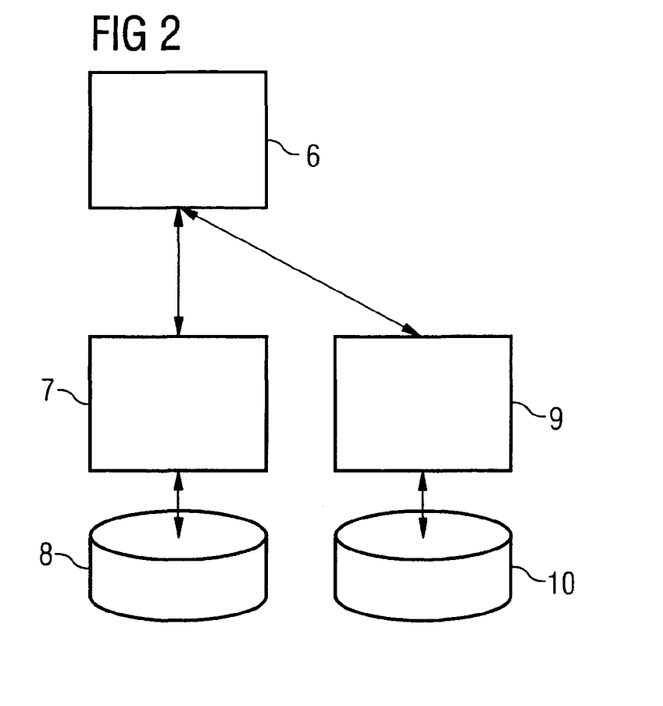
FIG. 2 diagrammatically represents the structure of an arrangement for performing the method according to an embodiment of the invention for creating and storing files having the data structure according to an embodiment of the invention.

FIG. 2 diagrammatically shows the structure of an arrangement which is suitable for performing the method according to an embodiment of the invention for creating and storing a first file which exhibits a file header and a file body.

In this figure, reference symbol 6 designates a device for creating files which, according to a preferred embodiment, exhibits a screen and a keyboard. As an alternative or additionally, a mouse or another input medium can also be provided.

The device for creating files 6 is connected to a device for storing and opening files 7.

The device for storing and opening files 7 can be, for example, a server which has a storage medium for files 8. As an alternative, the device for storing and opening files 7 can also be integrated in the device for creating files 6.

Furthermore, the device for creating files 6, according to the particularly preferred exemplary embodiment shown in FIG. 2, is connected to a coding device 9 which, in turn, is connected to a storage medium for coding rules 10.

Even if FIG. 2 shows separate storage media 8, 10 for the files and for the coding rules, it is also possible, as an alternative, to store files and coding rules on a common storage medium.

In the text which follows, the method for creating and storing a first file 1 which exhibits a file header 2 and a file body 3, is described with reference to FIGS. 1 and 2.

In a first step, the device for creating files 6 generates a file body 3 which contains the data to be stored in the first file 1, for example text or image data. Subsequently or at the same time, the device for creating files 6 generates a file header 2 which contains general information 4 with respect to the respective content of the respective file body 3 of the respective file 1, and stores the file body 3 together with the file header 2 as file 1 in the storage medium for files 8 via the device for storing and opening files 7.

During the generation or modification of the file body 3 of the first file 1, the device for creating files 6 automatically detects at least one access to a file body 3A, 3B, 3C of at least one further file 1A, 1B, 1C and stores the detected access or accesses as context information 5 in the file header 2 of the first file 1.

In the exemplary embodiment shown in FIG. 2, the context information 5 includes the file name and the storage location of the respective further file 1A, 1B and 1C and identifies the type of file body 3A, 3B, 3C (e.g. JPEG image, TXT text document, etc.) of the respective further file 1A, 1B, 1C.

In consequence, the method according to an embodiment of the invention ensures that each created or modified first file contains a reference to further files which were accessed during the creation of the first file.

Furthermore, the device for creating files 6 automatically reads out the general information 4A, 4B, 4C with respect to the respective content of the further file body 3A, 3B, 3C of the respective further referenced file 1A, 1B and 1C, which information is stored in a file header 3A, 3B, 3C of the at least one further file 1A, 1B, 1C, and stores the general information thus read out as additional context information 5 in the file header 2 of the first file 1 via the device for storing and opening files 7.

This ensures that the file header of the respective first file automatically contains information on the content of a referenced second file.

To obtain even more accurate knowledge of the content of the respective further file, the device for creating files 6 automatically reads out the data stored in a file body 3A, 3B, 3C of the at least one further file 1A, 1B, 1C and codes the data read out with the aid of the coding device 9 in accordance with a predetermined reference terminology which meets the SNOMED standard in the particularly preferred exemplary embodiment shown in FIG. 2 and is stored in the storage medium for coding rules 10.

Following this, the device for creating files 6 stores the data thus coded as additional context information 5 in the file header 2 of the first file 1 on the storage medium for files 8 with the aid of the device for storing and opening files 7.

The context information 5 of the first file 1 thus contains information on the content of the file body 3A, 3B, 3C of the respective referenced further file 1A, 1B, 1C in the form of a predetermined reference terminology which meets the SNOMED standard.

In order that a measure of the intensity of the material reference of the file body 3A, 3B, 3C of the respective further file 1A, 1B, 1C to the content of the file body 3 of the respective first file 1 is also specified, the device for creating files 6 is also constructed to determine a duration of a respective access to a file body 3A, 3B, 3C of at least one further file 1A, 1B, 1C during the generation or modification of the file body 3 of the first file 1 and automatically to store this duration as additional context information 5 in the file header 2 of the first file 1 in the storage medium for files 8 by way of the device for storing and opening files 7.

As an alternative or in addition, a measure of the intensity of the material reference (similarity) of the file body 3A, 3B, 3C of the respective referenced further file 1A, 1B, 1C to the content of file body 3 of the respective referencing first file 1 is also effected automatically by the device for creating files 6 by way of the information on the content of the respective referenced file 1A, 1B, 1C, stored in the context information 5 of the first file 1.

This requires that the information on the content of the respective referenced file 1A, 1B, 1C has been suitably coded by the coding device 9 and the similarity of different codes is stored in a predetermined similarity table.

This similarity table can be stored, for example, in the storage medium for coding rules 10 or directly in the device for creating files 6 in a solid-state memory.

The similarity measure thus determined by the device for creating files 6 by way of the similarity table can be stored in the context information 5 of the referencing first file 1 in addition to the other information relating to a respective referenced file 1A, 1B, 1C.

Figure 3A:
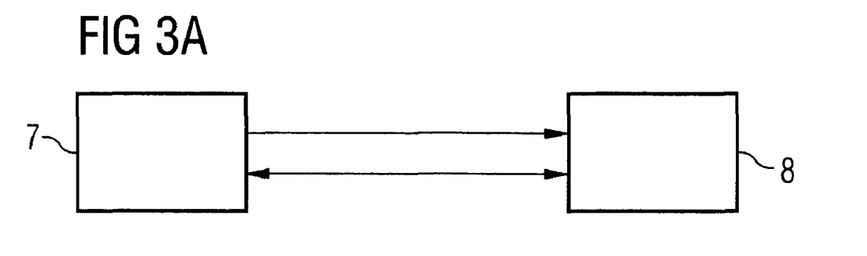
FIGS. 3a, 3b and 3c diagrammatically indicate various possibilities for searching for and accessing files stored in accordance with the data structure according to an embodiment of the invention.
Figure 3B:
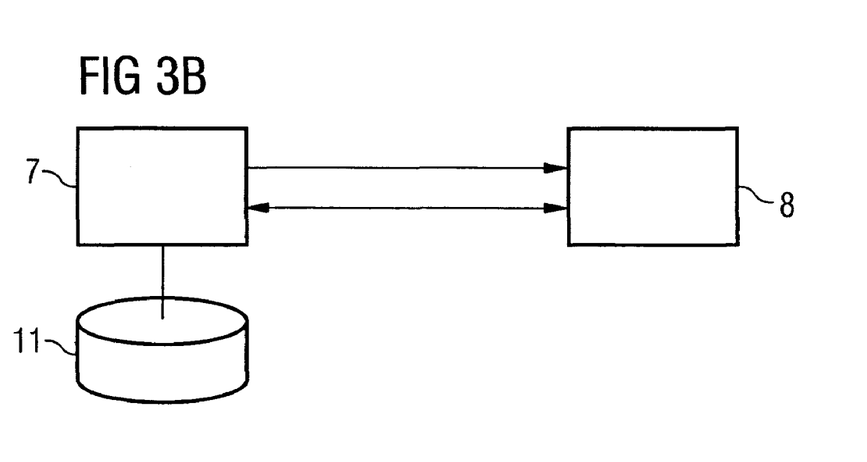
Figure 3C:
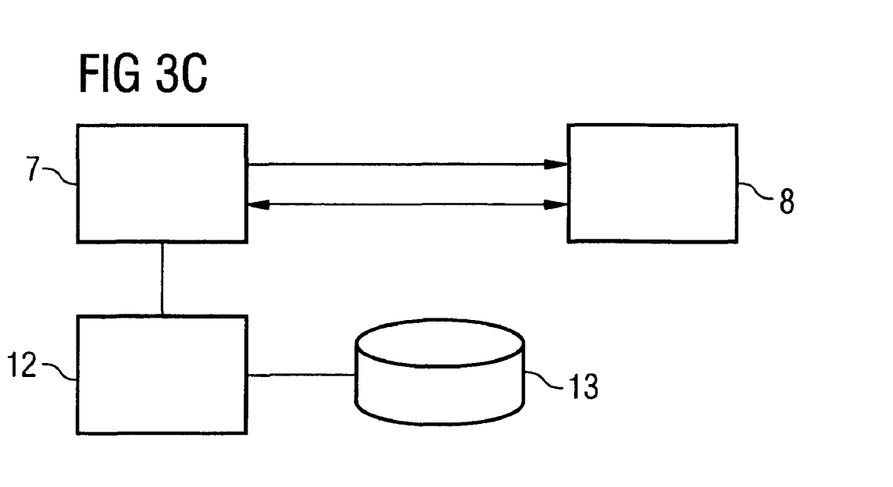

FIGS. 3a, 3b and 3c diagrammatically show various scenarios for storing and opening files according to the data structure according to an embodiment of the invention.

According to a first scenario shown in FIG. 3a, the files are manually stored (upper arrow) by a user by way of the device for storing and opening files 7 into the storage medium for files 8. The files are correspondingly opened (lower arrow) by searching for the file in the storage medium for files 8 and reading the file out of the storage medium for files 8.

The second scenario shown in FIG. 3b differs from the first scenario shown in FIG. 3a in that both the storing and the searching for files takes place in accordance with a configuration file which is stored in a storage medium for configuration files 11 connected to the device for storing and opening files 7. The configuration files stored in the storage medium for configuration data 11 contain predetermined storage/search instructions for particular types of files.

The third scenario shown in FIG. 3c differs from the first scenario shown in FIG. 3a in that the storing and searching for files takes place with the aid of a workflow manager 12 connected to the device for storing and opening files 7, which workflow manager, in turn, exhibits a storage medium for workflow rules 13.

The rules stored in the storage medium for workflow rules 13 prescribe particular search or storage rules for particular constellations of files. If the image currently being processed is, for example, an X-ray image of a body part of a patient, the associated workflow rule is to search for further image data of the same body part of the same patient and to store or to open these together with the new X-ray image. In this arrangement, storage is done by referencing in accordance with the data structure according to an embodiment of the invention. This ensures that referencings are also automatically created for existing data collections.

Figure 4:
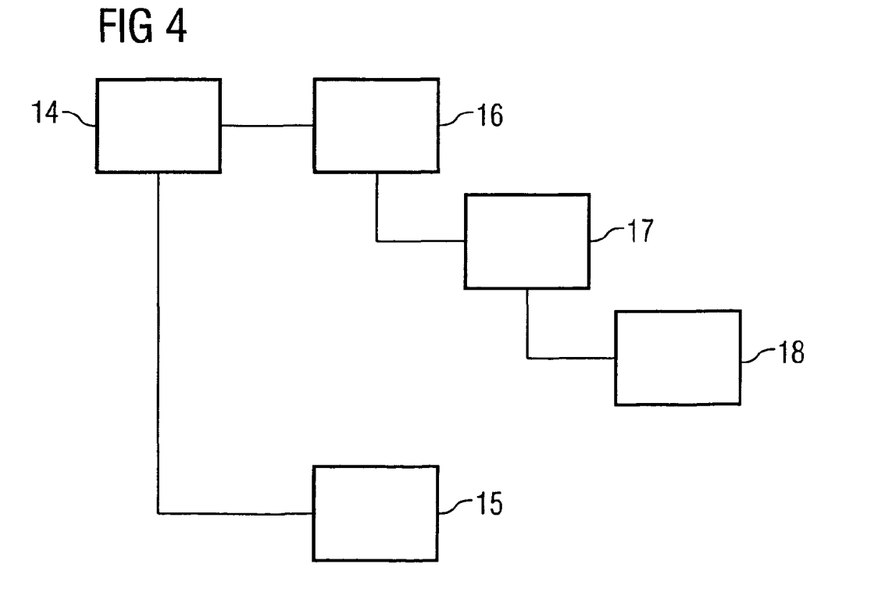
FIG. 4 shows the relationship between parameters which are used in the method according to an embodiment of the invention for the rule-based determination of files relevant in a respective current operating step.

FIG. 4 further illustrates the parameter used in the method according to an embodiment of the invention for the rule-based determination of files relevant in a respective current operating step by way of an actual example:

On the basis of an application context 15 of an application used for processing the currently processed file 1 (e.g. a program for digital image processing of an X-ray image or program for archiving medical data), the file header 2 of the file 1 currently processed by way of the application is analyzed. This can take place, for example, by way of the device for storing and opening files 7 shown in FIG. 2. In this process, the information on the content of the file body 3A, 3B, 3C of the respective referenced further files 1A, 1B, 1C, which information is stored in the context information 5 of the file header 2 of the currently processed file 1, is compared with the application context 15.

From the result of the analysis/comparison, the relevance of the further files 1A, 1B, 1C with respect to the application context 14 is automatically determined by way of the correspondence found. This can again be done by the device for storing and opening files 7.

In this process, the application context 14, as shown in FIG. 4, can be influenced by various other parameters such as, e.g. an observer context 15, a procedure context 16, an extended procedure context (not separately shown in FIG. 4), an operation step context 17 and a protocol context 18.

The observer context 16 is associated with a user of the currently processed file 1 and allows the selection of the further files 1A, 1B, 1C graded as relevant to be adapted to the habits and needs of a respective user.

If the user of the application is, for example, the gynecologist "Dr. Abel" with personnel number "154329", different files are usually relevant for satisfying the needs of this user than if the user of the application is gynecologist "Professor Mayer" with personnel number "123456".

The observer context 16 thus allows not only an adaptation to past habits of a user which can also be logged but also an adaptation of the further files 1A, 1B, 1C, to be graded as relevant, to the respective technical qualification of the current user.

The procedure context specifies the type of content of the file body of the currently processed file 1 (e.g. "CT thorax", code value "C-111"). The procedure context can be specified more or less accurately. Thus, an extended procedure context may also be provided such as e.g. "CT abdomen", code value "C-112".

To be able to take into consideration the type of operation to be performed by the application used, the application context is also influenced by the operating step context 17. A typical operating step context 17 is, for example, "check results", code value "C-1413".

The protocol context 18 is provided in order to be able to take into consideration the protocol used (e.g. "round lesion classification", code value "P-11213").

After determining the relevance of the further files 1A, 1B, 1C with respect to the application context 14, those referenced further files 1A, 1C are opened or interrogated and locally loaded (e.g. from other nodes such as a DICOM archive or information system) which have been estimated to be relevant in the current application context 14 due to the context information 5 stored in the file header 2 of the currently processed file 1.

For this purpose, the relevance found for the respective further file 1A, 1B, 1C is compared with a predetermined adjustable threshold value and only those further files 1A, 1C are automatically opened and/or interrogated and/or locally loaded, the relevance of which exceeds a predetermined threshold value.

In the text which follows, a pseudocode for the rule-based determination of files relevant in a respective current operating step is specified which refers to the exemplary embodiment shown in FIG. 4.

1) IF ("procedure context 16"="C-111" AND "operating step context 17"="C-1413") THEN "referenced file 1A, 1B, 1C" is_relevant (Boolean expression) IF "content of the context information 5 of file header 2 of the currently processed file 1"=("C-111" OR "C-112");
2) CHECK IF FILES GRADED AS is_relevant ARE LOCALLY AVAILABLE;
3) INTERROGATE THE FILES GRADED AS is_relevant WHICH ARE NOT LOCALLY AVAILABLE AND STORE THESE FILES LOCALLY.

Thus, firstly all referenced files relevant for the respective user of the application used for processing the currently processed file 1 are determined (in the example, both the referenced "CT thorax" and the referenced "CT abdomen" images are determined to be relevant by the rule for the checking of the results by "Dr. Abel" with personnel number "154329").

If the information on the content of the file bodies 3A, 3B, 3C of the respective further files 1A, 1B, 1C, which information is stored in the context information 5 of the file header 2 of the currently processed file 1, has values corresponding to the application context 14, the referenced files 1A, 1B, 1C are automatically graded as relevant or not relevant.

Even though the use of four parameters for determining the application context 14 is described in FIG. 4, this list is not conclusive. The application context 14 can be influenced by more or fewer or other parameters.

In summary, the information stored in the file header is automatically extended in accordance with the invention, in such a manner that each file contains detailed information on the context (e.g. procedure and clinical patient context) and associated relevant files.

As a result, an observer of a referencing file can determine why the referenced file was considered to be relevant at the time of creation of the first file without reading the respective file content of the referenced files. As a consequence, the workload is considerably reduced since now only referenced files appearing to be relevant need to be opened.

Furthermore, this provides for selective storage and retrieval of data relevant in the respective processing step with the aid of filtering functions. This shortens the time for searching for and selecting relevant data so that the preferably clinical data stored in a file can be assessed more rapidly.

Since the solution according to the invention is completely autonomous, it represents an advantageous alternative to an archiving system provided centrally on a server. This makes it possible to keep down the data traffic via any network which may be used and thus to shorten the transmission times.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer readable storage medium on which a data structure is stored, the data structure comprising:
a plurality of files including,
at least a first file and a second file, the first file including a first file header and a first file body, the first file header including information regarding content of the first file body, the first file header further including context information associated with at least the second file, the second file including a second file body having content relevant to the content of the first file body; wherein the context information is indicative of a specific basis for the relevance of the content of the second file to the content of the first file, and the specific basis indicates how or why the second file is relevant to the content of the first file, without the need to examine the content of the second file, the context information in the first file header includes at least one automatically detected access to the second file body, the automatic detection occurring during at least one of generation and modification of the first file body, and a name, storage location and specification of a type of the second file body is automatically stored as context information in the first file header, an access to the second file body being detected during generation or modification of the first file body.

2. The computer readable storage medium as claimed in claim 1, wherein the context information includes information corresponding to a predetermined reference terminology.

3. The computer readable storage medium as claimed in claim 2, wherein the reference terminology meets the SNOMED standard.

4. The computer readable storage medium as claimed in claim 1, wherein the context information includes a measure of the respective intensity of the material reference of the second file body of the second file to the content of the first file body of the first file.

5. The computer readable storage medium of claim 1, wherein the specific basis for the relevance of the content is an indication of a portion of the second file body deemed relevant to the content of the first file.

6. The computer readable storage medium of claim 1, wherein the content of the first file and the content of the second file is different.

7. A method for creating and storing a file on a computer readable storage medium, the method comprising:

generating a first file body including data to be stored in a first file;

generating a first file header including general information with respect to the content of the first file body of the first file;

storing the first file body together with the first file header in the first file;

automatically detecting at least one access to a second file body of at least a second file during at least one of the generation and modification of the first file body of the first file, the second file body having content relevant to the content of the first file body;

automatically storing the detected accesses as context information in the first file header of the first file, the context information being associated with the second file and being indicative of a specific basis for the relevance of the content of the second file to the content of the first file, the specific basis indicating how or why the second file is relevant to the content of the first file, without the need to examine the content of the second file; and storing the file on the computer readable storage medium; wherein the automatically storing includes, automatically storing, as context information in the first file header, a name, storage location and specification of a type of the second file body, an access to which was detected during generation or modification of the first file body.

8. The method as claimed in claim 7, wherein the context information includes information on the content of the second file body of the second file.

9. The method as claimed in claim 8, wherein the information on the content of the second file body of the second file is stored in the form of a predetermined reference terminology.

10. The method as claimed in claim 9, wherein the reference terminology meets the SNOMED standard.

11. The method as claimed in claim 7, wherein the method further comprises:

automatically reading out general information with respect to the respective content of the second file body of the second file, the information being stored in the second file header of the second file; and automatically storing the general information read out as additional context information in the first file header of the first file.

12. The method as claimed in claim 7, the method further comprising:

automatically reading out data stored in the second file body of the second file;

automatically coding the data read out in accordance with a predetermined reference terminology; and automatically storing the coded data as additional context information in the first file header of the first file.

13. The method as claimed in claim 7, the method further comprising:

automatically determining the duration of the respective access to the second file body of the second file during at least one of the generation and modification of the first file body of the first file; and automatically storing the particular duration of the respective access as additional context information in the first file header of the first file.

14. The method as claimed in claim 7, the method further comprising:

automatically comparing the information on the content of the second file body of the second file with an application context of an application used for processing a currently processed file;

automatically determining a relevance, resulting from the comparison, of the second file with respect to the application context; and at least one of automatically opening and locally loading the second file, the relevance of which exceeds a predetermined threshold value.

15. A computer readable storage medium storing a computer program, the computer program being adapted to, when executed on a computer, cause the computer to carry out the method as claimed in claim 7.

16. A computer program product, including the computer readable storage medium of claim 15.

* * * * *